(12) United States Patent
Martinez Ferreira et al.

(10) Patent No.: US 8,939,641 B2
(45) Date of Patent: Jan. 27, 2015

(54) X-RAY IMAGING APPARATUS HAVING VIBRATION STABILISING MEANS, AND METHOD FOR OPERATING SUCH AN X-RAY IMAGING APPARATUS

(75) Inventors: Carlos Martinez Ferreira, Buc (FR); Omar Al Assad, Buc (FR)

(73) Assignee: General Electric Company, Schenectady, NY (US)

( * ) Notice: Subject to any disclaimer, the term of this patent is extended or adjusted under 35 U.S.C. 154(b) by 286 days.

(21) Appl. No.: 13/481,083

(22) Filed: May 25, 2012

(65) Prior Publication Data
US 2013/0010925 A1    Jan. 10, 2013

(30) Foreign Application Priority Data

May 26, 2011   (EP) ..................................... 11305640

(51) Int. Cl.
*A61B 6/00*         (2006.01)
(52) U.S. Cl.
CPC ............... *A61B 6/4441* (2013.01); *A61B 6/547* (2013.01); *A61B 6/4476* (2013.01); *A61B 6/504* (2013.01)
USPC .......................................... 378/207; 378/197
(58) Field of Classification Search
CPC .... A61B 6/4441; A61B 6/4476; A61B 6/504; A61B 6/547; A61B 6/582
USPC .................................. 378/207, 196, 197, 198
See application file for complete search history.

(56) References Cited

U.S. PATENT DOCUMENTS

| | | | |
|---|---|---|---|
| 5,348,124 | A | 9/1994 | Harper |
| 5,548,653 | A | 8/1996 | Pla |
| 6,002,778 | A | 12/1999 | Rossetti |
| 6,454,303 | B2 | 9/2002 | Ashtiani |
| 6,644,590 | B2 | 11/2003 | Terpay |
| 6,959,484 | B1 | 11/2005 | Spangler |
| 7,586,236 | B2 | 9/2009 | Corsaro |
| 2005/0281391 | A1* | 12/2005 | Luo et al. ...................... 378/204 |

FOREIGN PATENT DOCUMENTS

| | | |
|---|---|---|
| JP | 2003245269 A | 9/2003 |
| JP | 2005027914 A | 2/2005 |

OTHER PUBLICATIONS

EP Search Report from corresponding EP Patent Application 11305640.2 Date as Aug. 19, 2010.

* cited by examiner

*Primary Examiner* — Glen Kao
(74) *Attorney, Agent, or Firm* — GE Global Patent Operation; Marc A. Vivenzio

(57) ABSTRACT

An X-ray imaging apparatus is provided. The X-ray imaging apparatus comprises an imaging assembly mounted on a rotary arm, the imaging assembly comprising an X-ray source and an X-ray detector coupled to the rotary arm so that X-rays emitted by the X-ray source are incidental to the X-ray detector. The X-ray imaging apparatus further comprises a first vibration measurement device coupled to the X-ray source and a second vibration measurement device coupled to the X-ray detector, and a first actuator and a second actuator configured to move the X-ray source and the X-ray detector to suppress at least one component of the vibrations measured by the first and second vibration measurement devices.

8 Claims, 3 Drawing Sheets

X-RAY IMAGING APPARATUS HAVING VIBRATION STABILISING MEANS, AND METHOD FOR OPERATING SUCH AN X-RAY IMAGING APPARATUS

BACKGROUND OF THE INVENTION

1. Field of the Invention

Embodiments of the present invention relate in general to medical imaging systems and, more particularly, to medical imaging systems minimizing the vibrations generated by such imaging systems when operated.

2. Description of the Related Art

Imaging systems usually comprise an imaging assembly comprising an X-ray source, namely an X-ray tube, and an X-ray detector placed opposite to the X-ray tube in a direction of emission of the X-rays. The tube and the detector are usually placed on two mutually opposite ends of a so-called "C-arm" shaped in the form of an arch.

During a radiographic examination, it is necessary to produce radiographs of a region of interest in the body of a patient irradiated by X-rays. For this purpose, after the patient has been laid out on an examination table, the X-ray tube and the detector are brought to face the region to be radiographed and to be centered around the region of interest.

When the X-ray chain, comprising the X-ray tube and the X-ray detector is moved to reach the region of interest, or when the X-ray chain is stopped, vibrations may appear in particular within the imaging assembly. However, the image quality and the perception of the image viewed by the operator are highly damaged when vibrations occur.

It is therefore desirable to eliminate the vibrations generated when the X-ray chain is moved to the region of interest or stopped.

Known vibration absorbers are utilized to control vibrations in an imaging system.

Some vibration control systems minimize the noise and/or vibrations generated by a magnetic resonance imaging (MRI) system, and are operated to create a secondary noise and/or vibration field which cancels the primary noise field generated when the MRI system is operated.

Magnetostrictive devices have also been used to prevent low frequency vibrations from propagating along an elongate member. Vibration isolation devices are utilized in various technical fields, for example within aircrafts or automotive vehicles.

Vibration absorbers, intended to absorb vibrations in the magnetic resonance imaging (MRI) system as a whole, have also been utilized. It has thus been noted that such vibration absorbers are not suitable to absorb efficiently the vibrations generated within an imaging assembly when moved to reach a region of interest or subsequently stopped.

In light of the foregoing, there is a need for an X-ray imaging apparatus and a method for operating such an X-ray imaging apparatus which remediates this drawback and suppresses the visible vibrations within the image.

BRIEF SUMMARY OF THE INVENTION

According to an embodiment, an X-ray imaging apparatus is provided. The X-ray imaging apparatus comprises an imaging assembly mounted on a rotary arm, the imaging assembly comprising an X-ray source and an X-ray detector coupled to the rotary arm so that X-rays emitted by the X-ray source are incidental to the X-ray detector. The X-ray imaging apparatus further comprises a first vibration measurement device coupled to the X-ray source and a second vibration measurement device coupled to the X-ray detector, and a first actuator and a second actuator configured to move the X-ray source and the X-ray detector to suppress at least one component of the vibrations measured by the first and second vibration measurement devices.

According to an embodiment, a method for operating an X-ray imaging apparatus is provided. The X-ray imaging apparatus comprises an imaging assembly mounted on a rotary arm, an X-ray source and an X-ray detector coupled to the rotary arm so that X-rays emitted by the X-ray source are incidental to the X-ray detector, a first vibration measurement device coupled to the X-ray source, a second vibration measurement device coupled to the X-ray detector, and a first and second actuator configured to move the X-ray source and the X-ray detector to suppress at least one component of vibrations measured by the first and second vibration measurement devices. The method comprises measuring vibration levels in the X-ray source and in the X-ray detector, and actuating the first and second actuators to move the X-ray source and the X-ray detector to suppress at least one component of the vibration levels.

BRIEF DESCRIPTION OF THE DRAWINGS

Other objects, features and advantages of the invention will appear on reading the following description, given only as a non-limiting example, and made with reference to the appended drawings, in which.

DETAILED DESCRIPTION OF THE INVENTION

The vibration control system disclosed in this document is in particular intended to minimize the noise and/or vibrations generated by a magnetic resonance imaging (MRI) system, and is operated to create a secondary noise and/or vibration field which cancels the primary noise field generated when the MRI system is operated.

Figure 1:
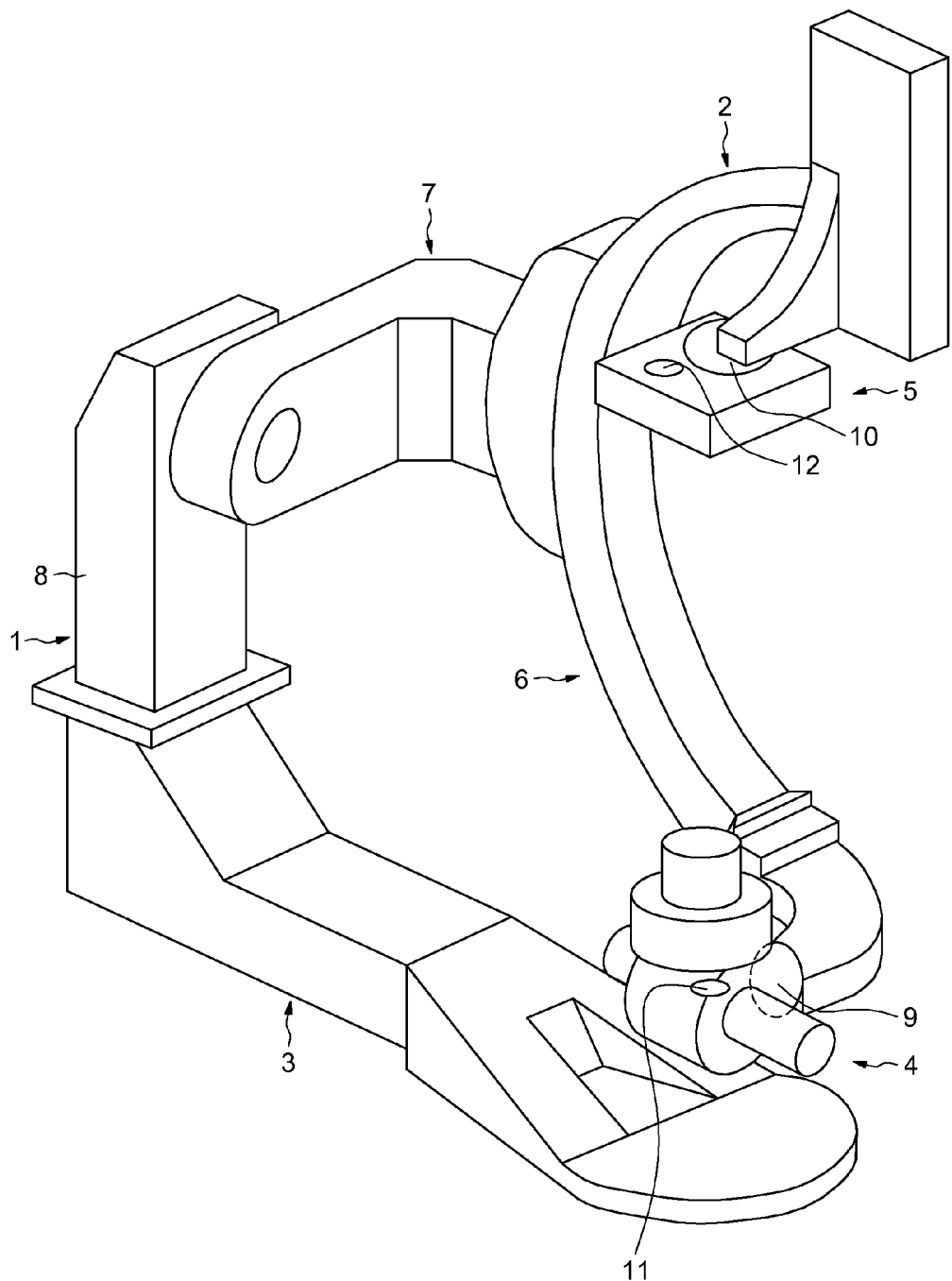
FIG. 1 is an isometric view of an X-ray imaging apparatus according to an embodiment of the invention.

FIG. 1 illustrates a medical imaging apparatus 1 according to an embodiment of the present invention, wherein the medical imaging apparatus 1 is of the vascular type. In this envisaged but non-limiting application, the imaging apparatus 1 is intended to be used for angiographic examination. As it can be seen, this apparatus 1 comprises an imaging assembly 2 mounted on a base assembly 3.

The imaging assembly 2 comprises an X-ray tube 4, capable of emitting a beam of X-rays in an emission direction, and an X-ray detector 5 placed at two mutually opposed ends of a C-arm 6, in this instance in the form of an arch, so that the X-rays emitted by the tube 4 are incident on the detector 5.

The arm 6 is mounted so as to slide on a second arm 7 mounted rotatingly on a fixed support 8, which is mounted on the base assembly 3.

Therefore, the support 8, the rotating arm 7 and the C-arm 6 are all three articulated relative to one another so that the X-ray imaging apparatus 1 can move in three dimensions so as to produce images of an organ to be examined from various angles.

During a radiography, the tube 4 and the detector 5 are brought to face a region of interest (ROI) in the body of a patient laid out on an examination table (not shown). When the region of interest is interposed between the X-ray tube 4 and the detector 5, it is irradiated by the X-rays, and the detector 5 produces data representative of characteristics of the interposed region of interest.

In order to suppress the vibrations generated by the imaging assembly 2 movements or residual vibrations generated when the imaging assembly 2 has reached its final position and is centered around the region of interest, the X-ray imaging apparatus 1 is further provided with one or more vibration measurement devices 11, 12 and one or more actuators 9, 10 operable to locally move the tube 4 and the detector 5, and to locally control their position.

As illustrated, in one embodiment, the imaging assembly 2 thus comprises at least two actuators 9, 10, one of the two actuators 9, 10 being associated with the tube 4 and the other of the two actuators 9, 10 being associated with the detector 5. The imaging assembly 2 also comprises at least two vibration measurement devices 11, 12, one of the two vibration measurement devices 11, 12 being associated with the tube 4 and the other of the two vibration measurement devices 11. 12 being associated with the detector 5.

The vibration measurement devices 11, 12 may be 3-axes measurement devices and may be directly attached to the tube 4 and to the detector 5, respectively.

The vibration measurement devices 11, 12 is configured to measure vibration levels in order to elaborate first and second control signals for the actuators 9, 10. It is understood that the vibration measurement devices 11, 12 may comprise, in at least one embodiment, different arrangements and may, for example, comprise two accelerometers mounted on the tube 4 and on the detector 5, respectively.

The actuators 9, 10 are coupled between the C-arm 6 and the tube 4 and the detector 5, respectively. They are mounted to the mutual opposite ends of the C-arm 6, in place of the rigid coupling used within the X-ray imaging apparatus according to the state of the art. The two actuators 9, 10 may be configured to locally move the tube 4 and the detector 5 to suppress the vibrations that may be visible within the image generated by the imaging assembly 2. By using vibration measurement devices 11, 12 and an actuator 9, 10 associated with the tube 4, on the one hand, and with the detector 5, on the other hand, it is possible to minimize vibrations in the tube 4 and in the detector 5, separately.

As can be conceived, the two actuators 9, 10 may also be of different arrangements. For example, in an embodiment, each actuator 9, 10 has piezoelectric properties, such that, when excited by the first and second control signals, it exerts a displacement force on the actuator 9. 10 to which it is attached.

In other words, the actuators 9, 10 may each comprise a piezoelectric actuator mounted to one end of the C-arm 6, and to which is attached the tube 4 or the detector 5, such that, when excited, the thickness of the actuators 9, 10 is modified in response to the first and second control signals and the position of the tube 4 and of the detector 5 can be modified in a way to suppress the visible vibrations.

Figure 2:
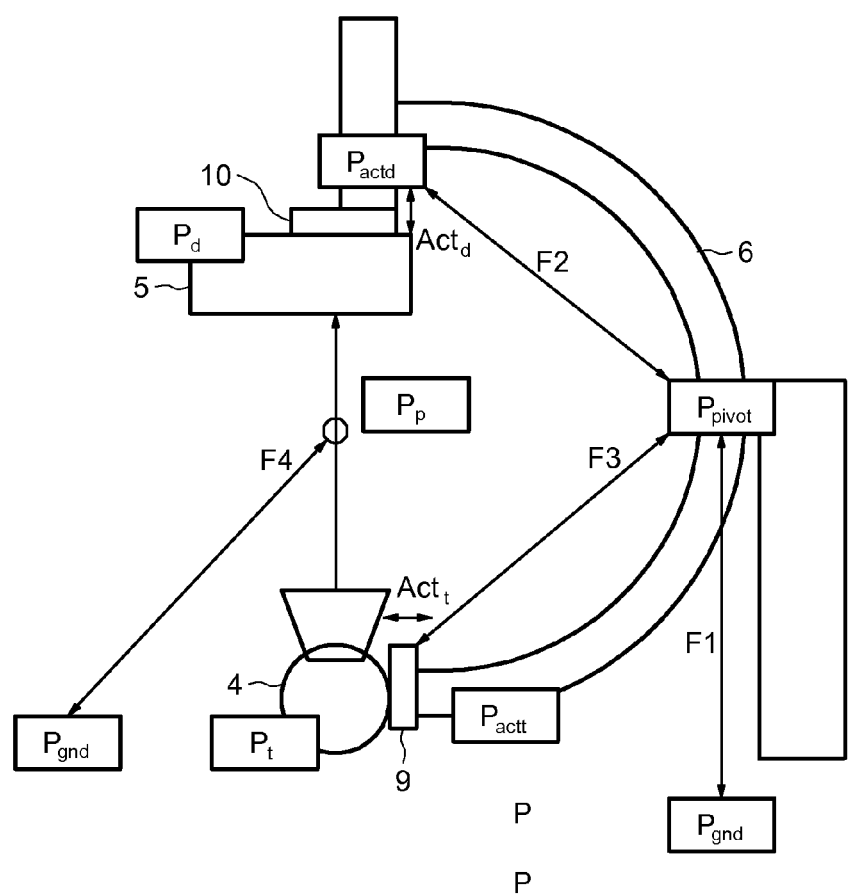
FIG. 2 is a schematic view of the X-ray imaging apparatus of FIG. 1, illustrating transfer functions used to elaborate the control signals for the actuators.

FIG. 2 illustrates that the X-ray imaging apparatus 1 may be provided with a set of sensors to measure the position of the significant elements of the apparatus 1. In particular, a sensor $P_d$ for measuring the position of the detector; a sensor $P_{actd}$ for measuring the position of the second actuator; a sensor $P_{pivot}$ for measuring the position of the knuckle of the C-arm 6; a sensor $P_p$ for measuring the position of the region of interest of the patient; a sensor $P_t$ for measuring the position of the tube; and a sensor $P_{actt}$ for measuring the position of the first actuator.

In addition, a set of transfer functions may be calculated by the vibration controller 14. In particular: a transfer function $F_1$ between the ground position $P_{gnd}$ and the knuckle position $P_{pivot}$; a transfer function $F_2$ between the knuckle position $P_{pivot}$ and the second actuator detector position $P_{actd}$; a transfer function $F_3$ between the knuckle position $P_{pivot}$ and the first actuator tube position $P_{actt}$; a transfer function $F_4$ between the ground position $P_{gnd}$ and the object position $P_p$; a transfer function $A_{ctt}$ between the tube position and the first actuator position $P_{actt}$; and a transfer function $A_{ctd}$ between the detector position $P_d$ and the second actuator position $P_{actd}$.

In other words, the transfer functions reads as follows:

$$P_{pivot} - P_{gnd} = F_1 \quad (1)$$

$$P_{Actd} - P_{pivot} = F_2 \quad (2)$$

$$P_{Actt} - P_{pivot} = F_3 \quad (3)$$

$$P_d - P_{Actd} = \text{Act}_d \quad (4)$$

$$P_t - P_{Acu} = \text{Act}_t \quad (5)$$

Taking as reference the ground, ($P_{gnd}=0$), the following transfer functions are obtained:

$$P_{Actd} - F_1 = F_2 \quad (6)$$

$$P_{Actt} - F_1 = F_3 \quad (7)$$

and:

$$P_d = \text{Act}_d + F_2 + F_1 \quad (8)$$

$$P_t = \text{Act}_t + F_3 + F_1 \quad (8)$$

In view of the foregoing, the variation Δi in the image due to vibrations may be defined by the following equation:

$$\Delta i = \Delta P_d + \Delta P_t \left( \frac{P_d - P_t}{P_p - P_t} \right) \quad (10)$$

such that:

$$\Delta i = \Delta [Act_d + F_2 + F_1] + \Delta [Act_t + F_3 + F_1] \left( \frac{P_d - P_t}{P_p - P_t} \right) \quad (11)$$

Figure 3:
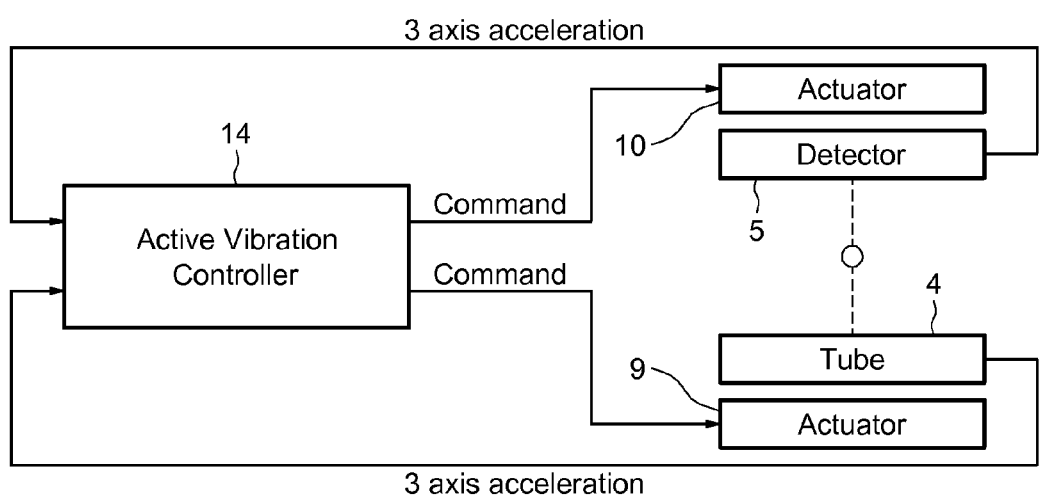
FIG. 3 is a schematic view of the vibration controller according to an embodiment of the invention.

It should be appreciated that, as illustrated by FIG. 3, the vibration levels on the tube 4 and detector 5 measured by the sensors $P_{Actd}$ and $P_{Actt}$ are used as feedback data to elaborate the first and second control signals "command" to move locally the tube 4 and the detector 5 and suppress the visible vibrations.

It should also be noted that a vibration controller 14 may be, for example, incorporated within a central processing unit. Such a central processing unit may be furnished with storage means, of data storage memory type, for example of the ROM, RAM, etc. . . . type, incorporating one or more control algorithm capable of moving the imaging assembly 2 relating to the base assembly 3. In particular, the rotation of the C-arm 6, either automatically or under the control of a control console (not shown), in response to instructions entered manually by an operator.

In view of the foregoing, the vibration controller calculates the transfer function $Act_t$ and $Act_d$ in order to minimize the image vibration cost function:

$$\min\left\{(Act_d + F_2 + F_1) + (Act_t + F_3 + F_1)\frac{P_d - P_t}{P_p - P_t}\right\} \quad (12)$$

Figure 4:
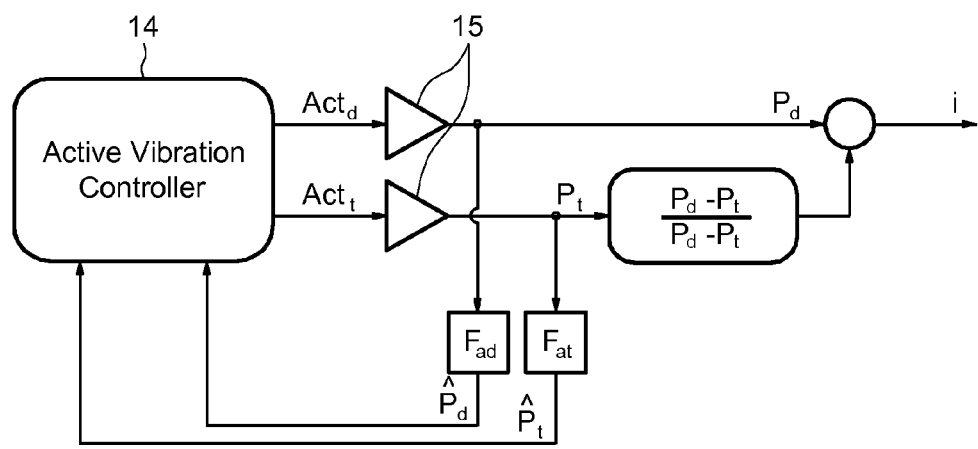
FIG. 4 illustrates a vibration image control diagram corresponding to the vibration suppression method carried out by a vibration controller according to an embodiment of the invention.

FIG. 4, which illustrates a control diagram carried out by the vibration controller to calculate equations (11) and (12), elaborates transfer functions $Act_d$ and $Act_t$ in order to minimize the vibration within the image and therefore, the variation in the image due to vibrations.

The calculated transfer functions are amplified by amplifiers 15 and 16 to generate the first and second control signals Fad and Fat used to drive the actuators 9, 10. As seen, an estimate $\hat{P}_d$ and $\hat{P}_t$ of the position of the tube 4 and of the detector 5 is used as a feedback loop by the vibration controller 14.

It will be understood that, by virtue of the imaging apparatus comprising a rotary arm and an imaging assembly mounted on the rotary arm and comprising an X-ray source and an X-ray detector coupled to the rotary arm so that the X-rays emitted by the X-ray source are incidental to the detector, and comprising first and second accelerometers coupled to the X-ray source and to the X-ray detector, respectively, and first and second piezoelectric actuators suitable for moving the X-ray source and the X-ray detector, it is possible to suppress at least one component of the vibrations measured by the first second accelerometers.

This written description uses examples of the subject matter disclosed to enable any person skilled in the art to practice the. same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. An X-ray imaging apparatus comprising:
an imaging assembly mounted on a rotary arm;
an X-ray source and an X-ray detector coupled to the rotary arm so that X-rays emitted by the X-ray source are incidental to the X-ray detector;
a first vibration measurement device coupled to the X-ray source and a second vibration measurement device coupled to the X-ray detector; and
a first piezoelectric actuator coupled between the rotary arm and the X-ray source and a second piezoelectric actuator coupled between the rotary arm and the X-ray detector, the first and second piezoelectric actuators configured so that, when actuated, a thickness of said actuators is modified to respectively move the X-ray source and the X-ray detector to suppress at least one component of vibrations measured by the first and second vibration measurement devices.

2. The X-ray imaging apparatus according to claim 1, wherein the first vibration measurement device comprises a first accelerometer and the second vibration measurement device comprises a second accelerometer.

3. The X-ray imaging apparatus according to claim 2, wherein the first accelerometer is mounted on the X-ray source and the second accelerometer is mounted on the X-ray detector.

4. The X-ray imaging apparatus according to claim 1, further comprising a vibration controller configured to receive vibration level measurements from the first and second vibration measurement devices, to generate first and second control signals based on the vibration level measurements, and to send the first and second control signals to the first and second piezoelectric actuators.

5. The X-ray imaging apparatus according to claim 4, wherein the vibration controller is configured to generate the first and second control signals to minimize the following function:

$$\Delta i = (Act_d + F_2 + F_1) + (Act_t + F_3 + F_1)\frac{P_d - P_t}{P_p - P_t} \quad (1)$$

wherein:
$\Delta i$ corresponds to image variation due to the vibrations;
$Act_d$ represents a difference of position between the X-ray detector and the second actuator;
$F_1$ corresponds to the position of a knuckle of the rotary arm;
$F_2$ corresponds to a difference of position between the second actuator and the knuckle of the rotary arm;
$Act_t$ represents a difference of position between the X-ray source and the first actuator;
$F_3$ represents a difference of position between the first actuator and the knuckle of the rotary arm;
$P_d$ corresponds to the position of the X-ray detector;
$P_t$ corresponds to the position of the X-ray source; and
$P_p$, corresponds to the position of a patient body to be imaged.

6. An X-ray imaging apparatus comprising:
an imaging assembly mounted on a rotary arm;
an X-ray source and an X-ray detector coupled to the rotary arm so that X-rays emitted by the X-ray source are incidental to the X-ray detector;
a first vibration measurement device coupled to the X-ray source and a second vibration measurement device coupled to the X-ray detector;
a first actuator and a second actuator configured to move the X-ray source and the X-ray detector to suppress at least one component of vibrations measured by the first and second vibration measurement devices; and
a vibration controller configured to receive vibration level measurements from the first and second vibration measurement devices, to generate first and second control signals based on the vibration level measurements, and to send the first and second control signals to the first and second actuators, wherein the vibration controller is configured to generate the first and second control signals to minimize the following function:

$$\Delta i = (Act_d + F_2 + F_1) + (Act_t + F_3 + F_1)\frac{P_d - P_t}{P_p - P_t} \quad (1)$$

wherein:
$\Delta i$ corresponds to image variation due to the vibrations;
$Act_d$ represents a difference of position between the X-ray detector and the second actuator;
$F_1$ corresponds to the position of a knuckle of the rotary arm;
$F_2$ corresponds to a difference of position between the second actuator and the knuckle of the rotary arm;
$Act_t$ represents a difference of position between the X-ray source and the first actuator;

$F_3$ represents a difference of position between the first actuator and the knuckle of the rotary arm;

$P_d$ corresponds to the position of the X-ray detector;

$P_t$ corresponds to the position of the X-ray source; and $P_p$ corresponds to the position of a patient body to be imaged.

7. The X-ray imaging apparatus according to claim 6, wherein the first actuator comprises a first piezoelectric actuator coupled between the rotary arm and the X-ray source, and the second actuator comprises a second piezoelectric actuator coupled between the rotary arm and the X-ray detector.

8. A method for operating an X-ray imaging apparatus comprising an imaging assembly mounted on a rotary arm, an X-ray source and an X-ray detector coupled to the rotary arm so that X-rays emitted by the X-ray source are incidental to the X-ray detector, a first vibration measurement device coupled to the X-ray source, a second vibration measurement device coupled to the X-ray detector, a first and second piezoelectric actuator configured to move the X-ray source and the X-ray detector to suppress at least one component of vibrations measured by the first and second vibration measurement devices, and a vibration controller, the method comprising:

measuring vibration levels in the X-ray source and in the X-ray detector;

generating, with the vibration controller, first and second control signals based on the measured vibration levels;

sending the first and second control signals to the first and second piezoelectric actuators; and modifying a thickness of the first and second piezoelectric actuators to move the X-ray source and the X-ray detector to suppress at least one component of the vibration levels.

* * * * *